US006790952B2

(12) United States Patent
Groen et al.

(10) Patent No.: US 6,790,952 B2
(45) Date of Patent: Sep. 14, 2004

(54) QUANTITATIVE EPSTEIN BARR VIRUS PCR RAPID ASSAY

(75) Inventors: Pamela A. Groen, Cincinnati, OH (US); David P. Witte, Cincinnati, OH (US)

(73) Assignee: Cincinnati Children's Hospital Research Foundation, Cincinnati, OH (US)

( * ) Notice: Subject to any disclaimer, the term of this patent is extended or adjusted under 35 U.S.C. 154(b) by 0 days.

(21) Appl. No.: 10/074,620

(22) Filed: Feb. 13, 2002

(65) Prior Publication Data

US 2003/0175684 A1 Sep. 18, 2003

Related U.S. Application Data

(60) Provisional application No. 60/268,439, filed on Feb. 13, 2001.

(51) Int. Cl.[7] .......................... C07H 21/00; C12P 19/30; C12P 19/34; C12Q 1/00; C12Q 1/68

(52) U.S. Cl. ................ 536/24.33; 536/24.3; 536/24.32; 536/23.1; 536/23.72; 435/4; 435/5; 435/6; 435/91.2

(58) Field of Search .............................. 536/24.3, 24.32, 536/29.33, 23.1, 23.72; 435/91.2

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 5,455,175 A | 10/1995 | Wittwer et al. | 435/286.1 |
| 5,807,522 A | 9/1998 | Brown et al. | 422/50 |
| 5,837,832 A | 11/1998 | Chee et al. | 536/22.1 |

FOREIGN PATENT DOCUMENTS

WO 9516028 A1 * 6/1995

OTHER PUBLICATIONS

Ausubel et al. Short Protocols in Molecular Biology, 1999, 4th Edition, Edited by Ausubel et al. Published by John Wiley & Son Inc., p. 6–6 to 6–8.*
Wetmur, J.G. Critical Reviews in Biochemistry and Molecular Biology 1991, vol. 26, pp. 227–259.*
A simple introduction to the science of the polymerase chain reaction, PCR: Basics for beginners, Jan. 31, 2001.
Adaptation Protocol for Sequence–Specific Detection of DNA with Hybridization Probes, Roche Molecular Biochemicals, Technical Note. No. Mar. 1999.
Antin, J. et al., Selective depletion of bone marrow T lymphocytes with anti–CD5 monoclonal antibodies: Effective prophylaxis for graft–vs–host disease in patients with hemtologic malignancies. Blood: 78: 2139, 1991.
Baldanti F, et al., Highlevels of Epstein–Barr virus DNA in blood of solid organ transplant recipients and their value in predicting posttransplant lymphoproliferative disorders. J. Clin Microbiol. 38: 613, 2000.
Caplin, et al., The most direct way to monitor PCR amplification for quantification and mutation detection, Roche Moelcular Biochemicals, Biochemica—No. 1, 1999.
Choice of Suitable Probe Targets, 1 page article.
DeSilva, et al., Rapid Genotyping and Quantification on the LightCycler™ with Hybridization Probes, Biochemica, No. 2, (1998).
Groen, Pamela, et al., "Development of a Quantitative EBV PCR Assay for the LightCycler System," 14 pgs, (2001).
Henry T., et al., Correlation of Epstein–Barr viral load with development of PTLD in solid organ transplant recipients. (In press). (Article Unavailable).
Ho M., et al. The frequency of Epstein–Barr virus infection and associated lymphoproliferative syndrome after transplantation and its manifestations in children, Transplantation 45: 719–727, 1988.
Kenagy DN, et al., Epstein–Barr virus DNA in peripheral blood leukocytes with post–transplant lymphoproliferative disease. Transplant 60:547, 1995.
Kimura H., et al., Quantitative analysis of Epstein–Barr virus load by using a real–time PCR assay. J. Clin Microbiol. 37:132, 1999.
Landt, et al., Selection of Hybridization Probe Sequences for Use with the LightCycler, Roche Molecular Biochemicals, Technical Note No. LC6/99.
LightCycler Principles, Biochem Boehringer–Mannheim.
Loechelt, Brett J., et al., "GM–CSF as Pre–Emptive Therapy for Post Transplant EBV Disease," 3 pgs, (2001).
Lucas KG, et al., Semiquantitative Epstein–Barr virus DNA in blood of solid organ transplant recipients and their value in predicting posttransplant lymphoproliferative disorders. J. Clin Microbiol. 38: 613, 2000. (Article Unavailable).
Martell, M., et al., High–throughput real–time reverse transcription–PCR quantitation of hepatitis C virus RNA. J. Clin. Microbiol. Feb. 1999: 37(2):327–32.

(List continued on next page.)

Primary Examiner—James Housel
Assistant Examiner—Baoqun Li
(74) Attorney, Agent, or Firm—Frost Brown Todd LLC

(57) ABSTRACT

The present invention provides novel compositions comprising Epstein-Barr virus-specific oligonucleotides that are useful as primers to amplify particular regions of the genome during enzymatic nucleic acid amplification. The invention also provides a rapid, sensitive and specific method for the detection and quantitation of the virus which may be present in a clinical specimen, using the virus-specific primers and enzymatic nucleic acid amplification; hybridization of amplified target sequences, if present, with one or more Epstein-Barr virus-specific oligonucleotide probes which are labeled with a detectable moiety; and detection of the detectable moiety of labeled oligonucleotide probe hybridized to amplified target sequences of Epstein-Barr virus DNA.

25 Claims, 1 Drawing Sheet

OTHER PUBLICATIONS

Martin, PJ, et al., *Fatal Epstein–Barr virus associated proliferation of donor B cells after treatment of acute graft vs–host disease with a murine anti–T–cell antibody*. Ann Intern Med 101:310, 1984.

Mercier B., et al., *Simultaneous screening for HBV DNA and HCV RNA genomes in blood donations using a novel Taq-Man PCR assay*. J. Cirol Methods, Jan. 1999: 77(1):1–9.

Niesters H, et al., *Development of a real–time quantitative assay for detection of Epstein–Barr virus*. J. Clin Microliol. Feb. 2000: 38(2):712–5.

Papdopoulos EB, et al., *Infusions of donor leukocytes as treatment of Epstein–Barr virus associated lymphoproliferative disorder complicating allogeneic marrow transplantation*, N. Engl J. Med 330: 1185, 1994.

Rasmussen et al., *Quantitative PCR by Continuous Fluorescence Monitoring of a Double Strand DNA Specific Binding Dye*, Biochemica, No. 2, (1998).

Recombinant DNA Technology, *DNA Amplification by the Polymerase Chain Reaction*, Chapter 3, Nucleotides and Nucleic Acids.

Riddler SA, et al., *Increased levels of circulating Epstein–Barr virus (EBV) infected lymphocytes and decreased EBV nuclear antigen antibody responses are associated with the development of post–transplant lymphoproliferative disease in solid–organ transplant recipients*. Blood 84:972, 1994.

Rogers B, et al., *Epstein–Barr virus polymerase chain reaction and serology in pediatric post–transplant lymphoproliferative disorder: three year experience*. Pediatric & Developmental Pathology 1: 480, 1998.

Savoie A, et al., *Direct correlation between the load of Epstein–Barr virus infected lymphocytes in the peripheral blood of pediatric transplant patients and risk of lymphoproliferative disease*. Blood 83: 2715, 1994.

Shapiro, RS, et al., *Epstein–Barr virus associated B–cell lymphoproliferative disorders following bone marrow transplantation*. Blood 71: 1234, 1988.

Starzl T, et al., *Reversibility of lymphomas and lymphoproliferative lesions development under cyclosporin steroid therapy*, Lancet I: 583, 1984.

*The LightCycler™—the Smartest Innovation for More Efficient PCR*, Biochemica, No. 2 (1998).

University of Chicago Cancer Research Center, DNA Sequencing Facility, *The Standard Primers*, Apr. 17, 1997 update.

Zutter MM, et al. *Epstein–Barr virus lymphoproliferation after bone marrow transplantation*. Blood 72, 520, 1988.

* cited by examiner

QUANTITATIVE EPSTEIN BARR VIRUS PCR RAPID ASSAY

This application claims the benefit of U.S. Provisional Patent Application Serial No. 60/268,439, filed Feb. 13, 2001, which application is hereby incorporated by reference in its entirety.

BACKGROUND OF THE INVENTION

The invention relates generally to novel compositions and methods for detecting the presence of viruses that frequently infect humans and are associated with the development of human disease. More particularly, the invention is directed to an accurate and sensitive method for the diagnosis and quantitation of Epstein-Barr virus infection using specific oligonucleotides as primers to amplify particular regions of the genome of the virus sought to be detected in a clinical specimen. Epstein-Barr virus-specific oligonucleotides may be used in the subsequent detection of the amplified regions of DNA.

Epstein-Barr virus (EBV), a human herpes virus, is ubiquitous in humans. Antibodies to polypeptides of the virus are present in over 80% of human serum samples from the United States and in even higher percentages from populations in Asia and Africa. Although it is prevalent throughout the world, the consequences of EBV infection vary among different populations. The virus is responsible for of infectious mononucleosis, a benign proliferation of infected B-lymphocytes, in Western countries and is implicated in Burkitt's lymphoma in Africa and nasopharyngeal carcinoma (NPC) in Asia. EBV can also cause acute and rapidly progressive B lymphoproliferative disease in severely immune compromised patients.

As a result of the immunosuppression necessary to maintain the function of transplanted organs, transplant patients are all at risk for developing EBV infection and therefore post transplant lymphoproliferative disorder (PTLD). However, the group at highest risk for this complication is the liver transplant population. This is because these patients are generally very young, frequently less than 5 years of age, and therefore they frequently have not yet been exposed to EBV and as a result do not have a natural immunity to the virus.

Approximately 50% of the transplanted population develop EBV infection during the post-transplant course, frequently symptomatic including PTLD. These patients therefore are a prime population for monitoring the development of EBV infection and its associated complications. Approximately 50% of these patients will develop EBV infection requiring monitoring of the peripheral blood EBV DNA levels.

Nationally there are between 450–500 liver transplants in pediatric patients. In those patients under 14 months of age approximately 75% of them develop EBV infections. These numbers do not include all the bone marrow, kidney, heart, and lung transplants in pediatric patients. And although there is a lower incidence of EBV lymphoproliferative complication in all of the adult transplant patients, there is a clinically significant incidence of this complication in these patients as well. The demand for this kind of patient monitoring therefore is high. Currently, there are a few recognized labs who provide quantitative EBV analyses.

EBV associated post-transplant lymphoproliferative disease (PTLD) is a major cause of morbidity and mortality for children and adults who undergo solid organ transplantation and bone marrow transplantation (Ho M, et al. The frequency of Epstein-Barr virus infection and associated lymphoproliferative syndrome after transplantation and its manifestations in children. Transplantation 45:719–727, 1988).

Patients who are EBV naïve and receive an organ from an EBV positive donor, especially those treated with anti-T-cell immunotherapy (anti-thymocyte globulin or monoclonal antibodies), are at high risk for developing PTLD. Infants and toddlers, who comprise 50% of the pediatric liver transplant population, are usually EBV naïve. More than 75% of patients at risk acquire the virus within the first year of life. Up to 15% of liver transplant recipients who are at high risk will develop PTLD. Consequently, the risk of infection and complication is substantial.

For children, especially those less than two years of age, PTLD is a critical factor affecting cost, graft function and quality of life. Attempts to treat these transplant patients with interferon, acyclovir, and anti-B cell monoclonal antibodies are generally not successful once an EBV infection has been established or reactivated (Papadopoulos E B, et al. Infusions of donor leukocytes as treatment of Epstein-Barr virus associated lymphoproliferative disorder complicating allogeneic marrow transplantation. N Engl J Med 330: 1185, 1994; Zutter M M, et al. Epstein-Barr virus lymphoproliferation after bone marrow transplantation. Blood 72, 520, 1988; Shapiro R S, et al. Epstein-Barr virus associated B-cell lymphoproliferative disorders following bone marrow transplantation. Blood 71: 1234, 1988; Antin J et al. Selective depletion of bone marrow T lymphocytes with anti-CD5 monoclonal antibodies: Effective prophylaxis for graft-vs-host disease in patients with hematologic malignancies. Blood: 78: 2139, 1991; Martin P J, et al. Fatal Epstein-Barr virus associated proliferation of donor B cells after treatment of acute graft vs-host disease with a murine anti-T-cell antibody. Ann Intern Med 101:310, 1984). A number of studies however have shown that PTLD may be reversible in solid-organ transplant recipients following reduction or discontinuation of immune suppression (Starzl T, et al. Reversibility of lymphomas and lymphoproliferative lesions developing under cyclosporin steroid therapy. Lancet I: 583, 1984).

Differences in levels of EBV DNA found in the peripheral blood post-transplant may distinguish which patients are at highest risk to develop EBV PTLD and therefore could permit earlier intervention in these patients. Previous studies have shown a correlation between levels of EBV DNA and the occurrence of EBV-PLTD in organ transplant patients (Kenagy D N, et al. Epstein-Barr virus DNA in peripheral blood leukocytes with post-transplant lymphoproliferative disease. Transplant 60: 547, 1995; Riddler S A, et al. Increased levels of circulating Epstein-Barr virus (EBV) infected lymphocytes and decreased EBV nuclear antigen antibody responses are associated with the development of post-transplant lymphoproliferative disease in solid-organ transplant recipients Blood 84: 972, 1994; Savoie A, et al. Direct correlation between the load of Epstein-Barr virus infected lymphocytes in the peripheral blood of pediatric transplant patients and risk of lymphoproliferative disease. Blood 83: 2715, 1994). These results suggest the potential benefit of monitoring EBV DNA levels in the peripheral blood of the transplant patients may be clinically useful in the management and possible preemptive intervention of the development of PTLD in these patients. As a result, a number of assays using a variety of approaches have been developed and reported for either semiquantitative or quantitative determination of EBV DNA levels.

Most of the semiquantitative assays are based on standard PCR analysis of a dilution series of patient samples compared to a known standard. While extremely useful, quantitative PCR can be very laborious to perform. Most of the difficulties arise because only a very small number of the cycles in a PCR reaction contain useful information. The early cycles have undetectable amounts of the DNA product and late cycles (plateau phase) are almost as uninformative. The PCR product is then detected by gel electrophoresis followed by ethidium bromide staining of the gel. The result is determined by the lowest dilution at which a band is visible (Lucas K G, et al. Semiquantitative Epstein-Barr virus polymerase chain reaction for the determination of patients at risk for EBV induced lymphoproliferative disease after stem cell transplantation. Blood 91: 3654, 1998; Baldanti F, et al. High levels of Epstein-Barr virus DNA in blood of solid organ transplant recipients and their value in predicting post-transplant lymphoproliferative disorders. J. Clin Microbiol. 38: 613, 2000; Rogers B, et al. Epstein-Barr virus polymerase chain reaction and serology in pediatric post-transplant lymphoproliferative disorder: three year experience. Pediatric & Developmental Pathology 1: 480, 1998). The quantification of the PCR and RT-PCR products is therefore based on an endpoint approach rather than using a kinetic approach. Since some labs use probe specific confirmation of their PCR products and others do not, the specificity and sensitivity of these assays are quite variable.

The standards used for the quantitative determinations also vary, and even the sample preparation differs as some assays base the results on the number of copies per ml of whole blood, others use the number of isolated white blood cells as the basis, while still other labs base the determination on extracted total DNA quantity.

More recently the introduction of "real-time" quantitative PCR analysis has been developed for the determination of EBV viral DNA levels (Niesters H et al. Development of a real-time quantitative assay for detection of Epstein-Barr virus. J Clin Microbiol. February 2000; 38(2):712–5). Real-time or kinetic PCR is a powerful method for determining the initial template copy number. The quantitative information in a PCR reaction comes from the few cycles where the amount of DNA grows logarithmically from barely above background to the plateau. Often only 6 to 8 cycles out of 40 will fall in this log-linear portion of the curve. Since the fluorescence signal is acquired during each cycle, data from the critical cycles can be captured, quantified and the fluorescence plotted against the cycle number.

This technology has improved the dynamic range in which samples can be analyzed quantitatively without dilution which reduces substantially the turnaround time and is much less labor intensive and less prone to technical errors due to less manipulation involved (Kimura H, et al. Quantitative analysis of Epstein-Barr virus load by using a real-time PCR assay. J. Clin Microbiol. 37:132, 1999; Martell M, et al. High-throughput real-time reverse transcription-PCR quantitation of hepatitis C virus RNA J Clin Microbiol. February 1999; 37(2):327–32; Mercier B, et al. Simultaneous screening for HBV DNA and HCV RNA genomes in blood donations using a novel TaqMan PCR assay. J Virol Methods. January 1999; 77(1):1–9). This latter approach provides the best opportunity to provide routine monitoring of the transplant patient population for early evidence of EBV infection. Early detection and recognition of patients at high risk for PTLD will provide opportunities for preemptive therapy rather than treating and managing the complications of advanced PTLD.

Therefore, it would be advantageous to have an accurate and sensitive method for the diagnosis and quantitation of Epstein-Barr virus infection in a clinical specimen.

STATEMENT OF THE INVENTION

It is an object of the present invention to disclose a nucleic acid sequences (oligonucleotides) useful as primers and/or probes in the detection of a Epstein-Barr virus in clinical specimens. Also, the present invention is directed to a method of detecting the presence of Epstein-Barr virus in a clinical specimen wherein the oligonucleotides of the present invention may be used to amplify target nucleic acid sequences of a Epstein-Barr virus that may be contained within a clinical specimen, and/or to detect the presence or absence of amplified target nucleic acid sequences of the Epstein-Barr virus. Respective oligonucleotides may be used to amplify and/or detect EBV and EBV nucleic acid sequences. By using the oligonucleotides of the present invention and according to the methods of the present invention, as few as one to ten copies of the Epstein-Barr virus genome may be detected.

One object of the present invention is to provide oligonucleotides that can be used as primers to amplify specific nucleic acid sequences of EBV.

Another object of the present invention is to provide oligonucleotides that can be used as probes in the detection of amplified specific nucleic acid sequences of EBV.

Among the nucleic acids provided herein are the nucleic acids whose sequence is provided in SEQ ID NO:1, SEQ ID NO:2, SEQ ID NO:3, SEQ ID NO:4, SEQ ID NO:5, SEQ ID NO:6, SEQ ID NO:7 OR SEQ ID NO:8, or a fragment thereof. Additionally, the invention includes mutant or variant nucleic acids of SEQ ID NO:1, SEQ ID NO:2, SEQ ID NO:3, SEQ ID NO:4, SEQ ID NO:5, SEQ ID NO:6, SEQ ID NO:7 or SEQ ID NO:8, or a fragment thereof, any of whose bases may be changed from the corresponding bases shown in SEQ ID NO:1, SEQ ID NO:2, SEQ ID NO:3, SEQ ID NO:4, SEQ ID NO:5, SEQ ID NO:6, SEQ ID NO:7 or SEQ ID NO:8, while still hybridizing to an EBV DNA sequence. The invention further includes the complement of the nucleic acid sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8, including fragments, derivatives, analogs and homologs thereof. The invention additionally includes nucleic acids or nucleic acid fragments, or complements thereto, whose structures include chemical modifications.

The invention also includes an oligonucleotide that includes a portion of the disclosed nucleic acids. For example, the oligonucleotide can be at least 10 nucleotides in length and include at least nine contiguous nucleotides of SEQ ID NO:1, SEQ ID NO:2, SEQ ID NO:3, SEQ ID NO:4, SEQ ID NO:5, SEQ ID NO:6, SEQ ID NO:7 or SEQ ID NO:8.

A further object of the present invention is to provide an accurate and sensitive method for detecting the presence of EBV that may be contained in clinical specimens by using the oligonucleotides disclosed to amplify and detect specific nucleic acid sequences of EBV.

Another object of the present invention is to provide oligonucleotides that can be used as primers to amplify specific nucleic acid sequences of EBV.

Another object of the present invention is to provide oligonucleotides that can be used as probes in the detection of amplified specific nucleic acid sequences of EBV.

Another object of the present invention is to provide oligonucleotides that can be used as primers to amplify DNA sequences from the EBNA2 region of the EBV genome.

A further object of the present invention is to provide an accurate and sensitive method for detecting the presence of EBV that may be contained in clinical specimens by using the oligonucleotides disclosed to amplify and detect specific nucleic acid sequences of EBV.

It is a further object of the invention to provide a kit for identifying or amplifying a gene encoding an Epstein-Barr virus polypeptide.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

Figure 1:
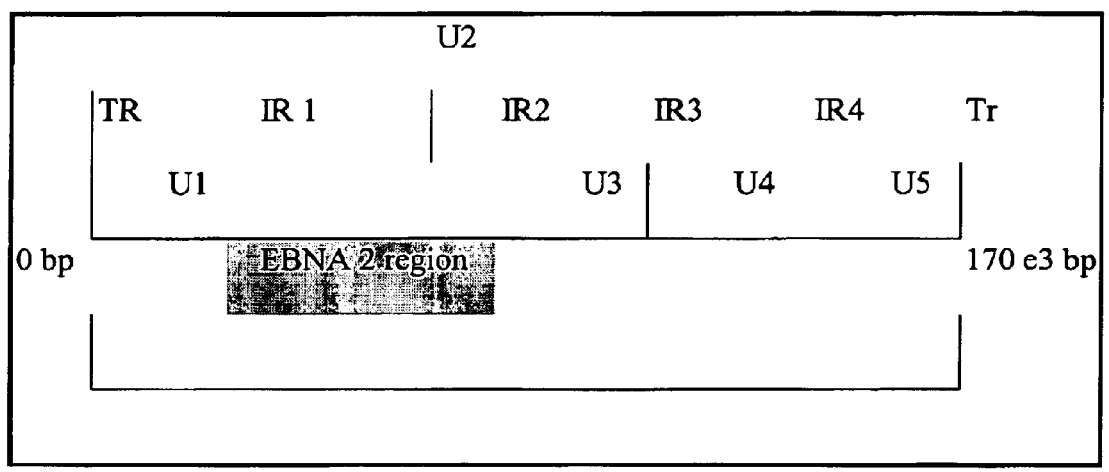
FIG. 1 is a diagrammatic representation of the Epstein-Barr Virus genomic map (GenBank Accession #K0333).

In the description that follows, a number of terms used in recombinant DNA technology are extensively utilized. In order to provide a clear and consistent understanding of the specification and claims, including the scope to be given such terms, the following definitions are provided.

An "amplification primer" is an oligonucleotide that is capable of annealing adjacent to a target sequence and serving as an initiation point for DNA synthesis when placed under conditions in which synthesis of a primer extension product which is complementary to a nucleic acid strand is initiated.

A "coding sequence" or "open reading frame" is a nucleotide sequence that is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA or RNA sequences. A polyadenylation signal and transcription termination sequence will usually be located 3' to the coding sequence.

By the term "complementarity" or "complementary" is meant, for the purposes of the specification or claims, a sufficient number in the oligonucleotide of complementary base pairs in its sequence to interact specifically (hybridize) with the target nucleic acid sequence of the Epstein-Barr virus to be amplified or detected. As known to those skilled in the art, a very high degree of complementarity is needed for specificity and sensitivity involving hybridization, although it need not be 100%. Thus, for example, an oligonucleotide that is identical in nucleotide sequence to an oligonucleotide disclosed herein, except for one base change or substitution, may function equivalently to the disclosed oligonucleotides. A "complementary DNA" or "cDNA" gene includes recombinant genes synthesized by reverse transcription of messenger RNA ("mRNA").

By the term "composition" is meant, for the purposes of the specification or claims, a combination of elements which may include one or more of the following: the reaction buffer for the respective method of enzymatic amplification, plus one or more oligonucleotides specific for Epstein-Barr virus, wherein said oligonucleotide is labeled with a detectable moiety.

By the terms "consisting essentially of a nucleotide sequence" is meant, for the purposes of the specification or claims, the nucleotide sequence disclosed, and also encompasses nucleotide sequences which are identical except for a one base change or substitution therein.

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time. Generally, a "cyclic polymerase-mediated reaction" includes primer molecules that serve to initiate synthesis of the complementary template, a polymerase enzyme that catalyzes the synthesis, and monomeric molecules that make up the template. In each cycle of a "cyclic polymerase-mediated reaction" not every template will necessarily by copied, and each complementary template whose synthesis is initiated in a cycle will not necessarily be completed. In preferred embodiments of this invention, the template and primer molecules are nucleic acids, the monomeric units are nucleotides, and the polymerase is a DNA or RNA polymerase.

"Denaturation" of a template molecule refers to the unfolding or other alteration of the structure of a template so as to make the template accessible to duplication. In the case of DNA, "denaturation" refers to the separation of the two complementary strands of the double helix, thereby creating two complementary, single stranded template molecules. "Denaturation" can be accomplished in any of a variety of ways, including by heat or by treatment of the DNA with a base or other denaturant.

A "detectable amount of product" refers to an amount of amplified nucleic acid that can be detected using standard laboratory tools. Generally, a "detectable amount of product" is between about 10 ng and about 100 ng of DNA. A "detectable marker" refers to a nucleotide analog that allows detection using visual or other means. For example, fluorescently labeled nucleotides can be incorporated into a nucleic acid during one or more steps of a cyclic polymerase-mediated reaction, thereby allowing the detection of the product of the reaction using, e.g. fluorescence microscopy or other fluorescence-detection instrumentation.

By the term "detectable moiety" is meant, for the purposes of the specification or claims, a label molecule (isotopic or non-isotopic) which is incorporated indirectly or directly into an oligonucleotide, wherein the label molecule facilitates the detection of the oligonucleotide in which it is incorporated when the oligonucleotide is hybridized to amplified Epstein-Barr virus sequences. Thus, "detectable moiety" is used synonymously with "label molecule". Synthesis of oligonucleotides can be accomplished by any one of several methods known to those skilled in the art. To label an oligonucleotide with a detectable moiety, detectable moiety-labeled dUTP may be added in the process of synthesizing the oligonucleotide so that the detectable moiety is incorporated directly into the oligonucleotide. Alternatively, the detectable moiety may be incorporated "indirectly" such as, for example, by biotinylating the 5' aminogroup of the oligonucleotide with sulfo-NHS-biotin.

Other label molecules, known to those skilled in the art as being useful for detection, include chemiluminescent or fluorescent molecules. Various fluorescent molecules are known in the art which are suitable for use to label a nucleic acid substrate for the method of the present invention. Fluorescent molecules used as labels may include amine-reactive molecules which are reactive to end terminal amines of the substrate; sulfonyl chlorides which are conjugated to the substrate through amine residues; and the like. Depending on the fluorescent molecule used, incorporating the substrate with the fluorescent molecule label include attachment by covalent or noncovalent means. The protocol for such incorporation may vary depending upon the fluorescent molecule used. Such protocols are known in the art for the respective fluorescent molecule.

"DNA amplification" as used herein refers to any process that increases the number of copies of a specific DNA sequence by enzymatically amplifying the nucleic acid sequence. A variety of processes are known. One of the most commonly used is the Polymerase Chain Reaction (PCR) process of Mullis as described in U.S. Pat. Nos. 4,683,195 and 4,683,202. PCR involves the use of a thermostable DNA polymerase, known sequences as primers, and heating cycles, which separate the replicating deoxyribonucleic acid (DNA), strands and exponentially amplify a gene of interest. Any type of PCR, such as quantitative PCR, RTPCR, hot start PCR, LAPCR, multiplex PCR, touchdown PCR, etc., may be used. Preferably, quantitative PCR is used. In general, the PCR amplification process involves an enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed.

"DNA" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

By the terms "enzymatically amplify" or "amplify" is meant, for the purposes of the specification or claims, DNA amplification, i.e., a process by which nucleic acid sequences are amplified in number. There are several means for enzymatically amplifying nucleic acid sequences. Currently the most commonly used method is the polymerase chain reaction (PCR).

Other amplification methods include LCR (ligase chain reaction) which utilizes DNA ligase, and a probe consisting of two halves of a DNA segment that is complementary to the sequence of the DNA to be amplified, enzyme QB replicase and a ribonucleic acid (RNA) sequence template attached to a probe complementary to the DNA to be copied which is used to make a DNA template for exponential production of complementary RNA; strand displacement amplification (SDA); Qβ replicase amplification (QβRA); self-sustained replication (3SR); and NASBA (nucleic acid sequence-based amplification), which can be performed on RNA or DNA as the nucleic acid sequence to be amplified.

The "extension of the primer molecules" refers to the addition of nucleotides to a primer molecule so as to synthesize a nucleic acid complementary to a template molecule. "Extension of the primer molecules" does not necessarily imply that the primer molecule is extended to synthesize a complete complementary template molecule. Rather, even if only a fraction of the template molecule has been copied, the primer is still considered extended.

A "fragment" of a molecule such as a protein or nucleic acid is meant to refer to any portion of the amino acid or nucleotide genetic sequence.

As used herein, "fluorescence resonance energy transfer pair" or "FRET pair" refers to a pair of fluorophores comprising a donor fluorophore and acceptor fluorophore, wherein the donor fluorophore is capable of transferring resonance energy to the acceptor fluorophore. In other words the emission spectrum of the donor fluorophore overlaps the absorption spectrum of the acceptor fluorophore. In preferred fluorescence resonance energy transfer pairs, the absorption spectrum of the donor fluorophore does not substantially overlap the absorption spectrum of the acceptor fluorophore. As used herein, "a donor oligonucleotide probe" refers to an oligonucleotide that is labeled with a donor fluorophore of a fluorescent resonance energy transfer pair. As used herein, "an acceptor oligonucleotide probe" refers to an oligonucleotide that is labeled with an acceptor fluorophore of a fluorescent resonance energy transfer pair. As used herein, "FRET oligonucleotide pair" refers to the donor oligonucleotide probe and the acceptor oligonucleotide probe pair that form a fluorescence resonance energy transfer relationship when the donor oligonucleotide probe and the acceptor oligonucleotide probe are both hybridized to their complementary target nucleic acid sequences. Two separate FRET oligonucleotide pairs, each specific for one locus and each comprising a different acceptor dye may be used at the same time. Acceptable fluorophore pairs for use as fluorescent resonance energy transfer pairs are well know to those skilled in the art and include, but are not limited to, fluorescein/rhodamine, phycoerythrin/Cy7, fluorescein/Cy5, fluorescein/Cy5.5, fluorescein/LC Red 640, and fluorescein/LC Red 705.

A "functional derivative" of a sequence, either protein or nucleic acid, is a molecule that possesses a biological activity (either functional or structural) that is substantially similar to a biological activity of the protein or nucleic acid sequence. A functional derivative of a protein may or may not contain post-translational modifications such as covalently linked carbohydrate, depending on the necessity of such modifications for the performance of a specific function. The term "functional derivative" is intended to include the "fragments," "segments," "variants," "analogs," or "chemical derivatives" of a molecule.

A "heterologous" region of a DNA or RNA construct is an identifiable segment of DNA or RNA molecule within a larger nucleic acid that is not found in association with the larger molecule in nature. For instance, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The term "hybridization" refers to the principle that two single-stranded nucleic acid molecules that have complementary base sequences will reform the thermodynamically favored double-stranded structure if they are mixed under the proper conditions. The double-stranded structure will be formed between two complementary single-stranded nucleic acids even if one is immobilized. The term "standard hybridization conditions" in general refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10–20° C. below the predicted or determined $T_m$ with washes of higher stringency, if desired. As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target sequence hybridize to the target sequence at equilibrium. Since the target sequences are generally present in excess, at $T_m$, 50% of the probes are occupied at equilibrium. Stringent conditions may also be achieved with the addition of destabilizing agents, such as formamide. Stringent conditions are known to those skilled in the art. Preferably, the conditions are such that sequences at least about 65%, 70%, 75%, 85%, 90%, 95%, 96%, 97%, 98%, or 99% homologous to each other typically remain hybridized to each other.

As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA. An "isolated" nucleic acid molecule is one that is separated from other nucleic acid molecules that are present in the natural source of the nucleic acid. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as primers or probes. Oligonucleotide means any nucleotide of more than 3 bases in length used to facilitate detection or identification of a target nucleic acid, including probes and primers.

A DNA sequence is "operatively linked" to an expression control sequence when the expression control sequence controls and regulates the transcription and translation of that DNA sequence. The term "operatively linked" includes having an appropriate start signal (e.g., ATG or AUG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

"PCR" refers to a polymerase chain reaction, which is a thermocyclic, polymerase-mediated, DNA amplification reaction. A PCR typically includes template molecules, oligonucleotide primers complementary to each strand of the template molecules, a thermostable DNA polymerase, and deoxyribonucleotides, and involves three distinct processes that are multiply repeated to effect the amplification of the original nucleic acid. The three processes (denaturation, hybridization, and primer extension) are often performed at distinct temperatures, and in distinct temporal steps. In many embodiments, however, the hybridization and primer extension processes can be performed concurrently. The nucleotide sample to be analyzed may be PCR amplification products provided using the rapid cycling techniques described in U.S. Pat. No. 5,455,175.

A "polymerase" is an enzyme that catalyzes the sequential addition of monomeric units to a polymeric chain, or links two or more monomeric units to initiate a polymeric chain. In preferred embodiments of this invention, the "polymerase" will work by adding monomeric units whose identity is determined by and which is complementary to a template molecule of a specific sequence. For example, DNA polymerases such as DNA pol 1 and Taq polymerase add deoxyribonucleotides to the 3' end of a polynucleotide chain in a template-dependent manner, thereby synthesizing a nucleic acid that is complementary to the template molecule.

"Primer" means an oligonucleotide comprised of more than three deoxyribonucleotide used in amplification. Its exact length will depend on many factors relating to the ultimate function and use of the oligonucleotide primer, including temperature, source of the primer and use of the method. The primer can occur naturally (as a purified fragment or restriction digestion) or be produced synthetically. The primer is capable of acting as an initiation point for synthesis, when placed under conditions that induce synthesis of a primer extension product complementary to a nucleic acid strand. The conditions can include the presence of nucleotides and an inducing agent such as a DNA polymerase at a suitable temperature and annealing and extension times as well as the appropriate buffer (pH, magnesium chloride ($MgCl_2$) and potassium chloride ($KCl_2$) concentrations, and adjuncts). In the preferred embodiment the primer is a single-stranded oligodeoxyribonucleotide of sufficient length to prime the synthesis of an extension product from a specific sequence in the presence of an inducing agent. In the present application in the preferred embodiment the oligonucleotide primer typically contains about 10 to about 35 or more nucleotides, although it may contain fewer nucleotides. More particularly, primers may contain about 15 to about 30 nucleotides, preferably primers may contain about 18 to about 26 nucleotides. Sensitivity and specificity of the oligonucleotide primers are determined by the primer length and uniqueness of sequence within a given sample of a template DNA. Primers that are too short, for example, less than 10 mer may show non-specific binding to a wide variety of sequences in the genomic DNA and thus are not very helpful. Each primer pair herein is selected to be substantially complementary to the different strands of each specific NTS region to which the primer pairs bind. Thus one primer of each pair is sufficiently complementary to hybridize with a part of the sequence in the sense strand and the other primer of each pair is sufficiently complementary to hybridize with a different part of the same repetitive sequence in the anti-sense strand. The primer may be either single-stranded or double-stranded and must be sufficiently long to prime the synthesis of the desired extension product in the presence of the inducing agent. The exact length of the primer will depend upon many factors, including temperature and use of the method.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

"Probes" refer to nucleic acid sequences of variable length, preferably at least about 10 nucleotides (nt), but can be about 100 nt, or as many as about, e.g., 6,000 nt, depending on use. Probes typically contain about 10 to about 35 or more nucleotides, although it may contain fewer nucleotides. More particularly, probes may contain about 15 to about 30 nucleotides, preferably probes may contain about 18 to about 26 nucleotides. Probes are used in the detection of identical, similar, or complementary nucleic acid sequences by hybridization. Longer length probes are usually obtained from a natural or recombinant source, are highly specific and much slower to hybridize than oligomers. An oligonucleotide sequence used as a detection probe may be labeled with a detectable moiety. Various labeling moieties are known in the art. Said moiety may, for example, either be a radioactive compound, a detectable enzyme (e.g. horse radish peroxidase (HRP)) or any other moiety capable of generating a detectable signal such as a calorimetric, fluorescent, chemiluminescent or electrochemiluminescent signal. Preferred analysis systems wherein said labels are used are electrochemiluminescence (ECL) based analysis or enzyme linked gel assay (ELGA) based analysis. After hybridization with a detectable amount of product, the detectable moiety may be detected using known methods. Generally, the amount of detectable moiety is detected and the measured amount is then correlated to the amount of target DNA present. Preferably, the methods of the present invention additionally comprise adding an internal standard to the DNA amplification composition for assessing the relative amounts of EBV present after amplification. As already indicated above, and will be presented in the experimental part of the description, both the sensitivity and reliability of EBV mRNA detection is greatly improved using the oligonucleotides according to the present invention when compared to known oligonucleotides used in this art.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the –10 and –35 consensus sequences. Promoter sequences can also be used to refer to analogous RNA sequences or structures of similar function in RNA virus replication and transcription.

A "thermocyclic reaction" is a multi-step reaction wherein at least two steps are accomplished by changing the temperature of the reaction.

A "thermostable polymerase" refers to a DNA or RNA polymerase enzyme that can withstand extremely high temperatures, such as those approaching 100° C. Often, thermostable polymerases are derived from organisms that live in extreme temperatures, such as *Thermus aquaticus*. Examples of thermostable polymerases include, Taq, Tth, Pfu, Vent, deep vent, UlTma, and variations and derivatives thereof.

One embodiment of the present invention is directed to a nucleic acid sequences (oligonucleotides) useful as primers and/or probes in the detection of a Epstein-Barr virus in clinical specimens. Also, the present invention is directed to a method of detecting the presence of Epstein-Barr virus in a clinical specimen wherein the oligonucleotides of the present invention may be used to amplify target nucleic acid sequences of a Epstein-Barr virus that may be contained within a clinical specimen, and/or to detect the presence or absence of amplified target nucleic acid sequences of the Epstein-Barr virus. Respective oligonucleotides may be used to amplify and/or detect EBV and EBV nucleic acid sequences. By using the oligonucleotides of the present invention and according to the methods of the present invention, as few as one to ten copies of the Epstein-Barr virus genome may be detected in the presence of milligram quantities of extraneous DNA.

One embodiment of the present invention is directed to EBV-specific oligonucleotides that can be used to amplify sequences of EBV DNA, and to subsequently determine if amplification has occurred, from DNA extracted from a clinical specimen. A pair of EBV-specific DNA oligonucleotide primers are used to hybridize to EBV genomic DNA that may be present in DNA extracted from a clinical specimen, and to amplify the specific segment of genomic DNA between the two flanking primers using enzymatic synthesis and temperature cycling. Each pair of primers are designed to hybridize only to the EBV DNA to which they have been synthesized to complement; one to each strand of the double-stranded DNA. Thus, the reaction is specific even in the presence of microgram quantities of heterologous DNA. For the purposes of this description, the primer derived from the sequence of the positive strand of DNA will be referred to as the "positive (+) primer", and the primer derived from the sequence of the negative strand will be referred to as the "negative (−) primer".

In one embodiment, the present invention relates to a composition for the detection of Epstein-Barr virus, consisting essentially of at least one purified and isolated oligonucleotide consisting of a nucleic acid sequence which complements and specifically hybridizes to an Epstein-Barr virus nucleic acid molecule, wherein said sequence is selected from the group consisting of SEQ. ID. NO. 1, SEQ ID NO. 2, SEQ. ID. NO. 5, SEQ.ID. NO. 6, and a nucleotide sequence which differs from SEQ. ID. NO. 1, SEQ ID NO. 2, SEQ. ID. NO. 5, or SEQ.ID. NO. 6 by a one base change or substitution therein.

An isolated and purified oligonucleotide primer pair for enzymatic amplification of Epstein-Barr virus DNA, consisting essentially of a pair of nucleic acid sequences which complement and specifically hybridize to an Epstein-Barr virus nucleic acid molecule, wherein said pair of nucleic acid sequences is selected from the group consisting of SEQ. ID. NO. 3, SEQ. ID. NO. 4, SEQ. ID. NO. 7, SEQ. ID. NO.8, and a nucleotide sequence which differs from SEQ. ID. NO. 3, SEQ. ID. NO. 4, SEQ. ID. NO. 7, or SEQ. ID. NO.8 by a one base change or substitution therein.

In another embodiment, the present invention relates to a method of detecting the presence of Epstein Barr virus in a sample comprising a) contacting the sample with the above-described nucleic acid probe, under conditions such that hybridization occurs, and b) detecting the presence of the probe bound to the DNA segment.

In another embodiment, the present invention relates to a method of detecting the presence of Epstein Barr virus in a sample comprising a) contacting the sample with the above-described nucleic acid probe, under conditions such that hybridization occurs, and b) detecting the presence of the probe bound to the DNA segment.

In another embodiment, the present invention relates to a method of detecting the presence of Epstein Barr virus in a sample comprising a) contacting the sample with the above-described nucleic acid probe, under conditions such that hybridization occurs, b) enzymatically amplifying a specific region of the EBV nucleic acid molecules, and c) detecting the presence of the probe bound to the DNA segment.

In another embodiment, the present invention relates to a method of detecting the presence of Epstein Barr virus in a sample comprising a) contacting the sample with the oligonucleotide primer pair of SEQ. ID. NO. 1 and SEQ ID NO. 2 or the oligonucleotide pair of SEQ. ID. NO. 5 and SEQ.ID. NO. 6 what under suitable conditions permitting hybridization of the oligonucleotides to the nucleic acid molecules of the EBV, b) enzymatically amplifying a specific region of the EBV nucleic acid molecules using the oligonucleotide pair of SEQ. ID. NO. 1 and SEQ ID NO. 2 or the oligonucleotide pair of SEQ. ID. NO. 5 and SEQ.ID. NO. 6 to form nucleic acid amplification products, c) contacting the amplified target sequences from step be, is present, with hybridization probes comprising the oligonucleotide pair of SEQ. ID. NO. 3 and SEQ. ID. NO. 4 or the oligonucleotide pair of SEQ. ID. NO. 7 and SEQ. ID. NO.8, labeled with a detectable moiety under suitable conditions permitting hybridization of the labeled oligonucleotide probe to amplified target sequences, and d) detecting the presence of amplified target sequences by detecting the detectable moiety of the labeled oligonucleotide probe hybridized to amplified target sequences. In a preferred embodiment, prior to performing the above method, the sample is treated to release nucleic acid molecules from cells in the sample. In another preferred embodiment, the presence of the amplified target sequences hybridized labeled oligonucleotide probe correlates to the presence of Epstein Barr virus in the sample.

In one embodiment, the method involves amplifying DNA sequences from the EBNA2 region of the EBV genome.

Any one of the methods commercially available may accomplish amplification of DNA. For example, the polymerase chain reaction may be used to amplify the DNA. Once the primers have hybridized to opposite strands of the target DNA, the temperature is raised to permit replication of the specific segment of DNA across the region between the two primers by a thermostable DNA polymerase. Then the reaction is thermocycled so that at each cycle the amount of DNA representing the sequences between the two primers is doubled, and specific amplification of the EBV DNA sequences, if present, results.

Further identification of the amplified DNA fragment, as being derived from EBV DNA, may be accomplished by liquid hybridization. This method utilizes one or more oligonucleotides labeled with detectable moiety as probes to specifically hybridize to the amplified segment of EBV DNA. Detection of the presence of sequence-specific amplified EBV DNA may be accomplished by simultaneous detection of the complex comprising the labeled oligonucleotide hybridized to the sequence-specific amplified EBV DNA ("amplified target sequences") with respect to the DNA amplification. Detection of the presence of sequence-specific amplified EBV DNA may also be accomplished using a gel retardation assay with subsequent detection of the complex comprising the labeled oligonucleotide hybridized to the sequence-specific amplified EBV DNA.

In such a enzymatic amplification reaction hybridization system of EBV detection, a clinical specimen of blood, CSF, amniotic fluid, urine, body secretions, or other body fluid is subjected to a DNA extraction procedure. High molecular weight DNA, including Epstein-Barr virus DNA, may be purified from blood cells, tissue cells, or virus particles (collectively referred to herein as "cells") contained in the clinical specimen using proteinase (proteinase K) extraction and ethanol precipitation. DNA may be extracted from a clinical specimen using other methods known in the art. Then, for example, the DNA extracted from the clinical specimen is enzymatically amplified in the polymerase chain reaction using EBV-specific oligonucleotides (SEQ ID NO:1 & SEQ ID NO:2; or SEQ ID NO:5 & SEQ ID NO:6) as primer pairs. Following amplification, EBV-specific oligonucleotides (SEQ ID NO:3 or SEQ ID NO:4, for use with SEQ ID NOs:1 & 2; or SEQ ID NO:7 or SEQ ID NO:8, for use with SEQ ID NOs:3 & 4) labeled with an appropriate detectable label are hybridized to the amplified target sequences, if present.

The contents of the hybridization reaction are then analyzed for detection of the sequence-specific amplified EBV DNA, if present in the DNA extracted from the clinical specimen. Thus, the oligonucleotides of the present invention have commercial applications in diagnostic kits for the detection of EBV DNA in clinical specimens.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample that is compatible with the method utilized.

In a related embodiment of the present invention, the EBV-specific oligonucleotides may be used to amplify and detect EBV DNA from DNA extracted from a clinical specimen. In this embodiment, the oligonucleotides used as primers may be labeled directly with detectable moiety, or synthesized to incorporate the label molecule. Depending on the label molecule used, the amplification products can then be detected, for example, after binding onto an affinity matrix, using isotopic or calorimetric detection.

In a preferred embodiment of this invention, cyclic polymerase-mediated reactions are performed. In certain embodiments of this invention, these processes are accomplished by changing the temperature of the solution containing the templates, primers, and polymerase. In such embodiments, the denaturation step is typically accomplished by shifting the temperature of the solution to a temperature sufficiently high to denature the template. In some embodiments, the hybridization step and the extension step are performed at different temperatures. In other embodiments, however, the hybridization and extension steps are performed concurrently, at a single temperature.

In some embodiments, the cyclic polymerase-mediated reaction is performed at a single temperature, and the different processes are accomplished by changing non-thermal properties of the reaction. For example, the denaturation step can be accomplished by incubating the template molecules with a basic solution or other denaturing solution.

In preferred embodiments, the percentage of template molecules that are duplicated in the cycle steps is e.g. 90%, 70%, 50%, 30%, or less. Such cycles may be as short as 8–10, 6, 5, 4.5, 4, 2, 1, 0.5 minutes or less. In certain embodiments, the reaction comprises 2, 5, 10, 15, 20, 30, 40, 50, or more cycles.

Typically, the reactions described herein are repeated until a detectable amount of product is generated. Often, such detectable amounts of product are between about 10 ng and about 100 ng, although larger quantities, e.g. 200 ng, 500 ng, 1 mg or more can also, of course, be detected. In terms of concentration, the amount of detectable product can be from about 0.01 pmol, 0.1 pmol, 1 pmol, 10 pmol, or more.

Oligonucleotides for use as primers, e.g., in PCR or non-thermal amplification reactions, are typically synthesized chemically according to the solid phase phosphoramidite triester method, e.g., using an automated synthesizer. Oligonucleotides can also be custom made and ordered from a variety of commercial sources known to persons of skill. Purification of oligonucleotides, where necessary, is typically performed by either native acrylamide gel electrophoresis or by anion-exchange HPLC.

Any of a variety of polymerases can be used in the present invention. For thermocyclic reactions, the polymerases are thermostable polymerases such as Taq, KlenTaq, Stoffel Fragment, Deep Vent, Tth, Pfu, Vent, and UlTma, each of which are readily available from commercial sources. Similarly, guidance for the use of each of these enzymes can be readily found in any of a number of protocols found in guides, product literature, and other sources.

For non-thermocyclic reactions, and in certain thermocyclic reactions, the polymerase will often be one of many polymerases commonly used in the field, and commercially available, such as DNA pol 1, Klenow fragment, T7 DNA polymerase, and T4 DNA polymerase. Guidance for the use of such polymerases can readily be found in product literature and in general molecular biology guides.

Those of skill in the art are aware of the variety of nucleotides available for use in the present reaction. Typically, the nucleotides will consist at least in part of deoxynucleotide triphosphates (dNTPs), which are readily commercially available. Parameters for optimal use of dNTPs are also known to those of skill, and are described in the literature. In addition, a large number of nucleotide derivatives are known to those of skill and can be used in the present reaction. Such derivatives include fluorescently labeled nucleotides, allowing the detection of the product including such labeled nucleotides, as described below. Also included in this group are nucleotides that allow the sequencing of nucleic acids including such nucleotides, such as dideoxynucleotides and boronated nuclease-resistant nucleotides, as described below. Other nucleotide analogs include nucleotides with bromo-, iodo-, or other modifying groups, which groups affect numerous properties of resulting nucleic acids including their antigenicity, their replicatability, their melting temperatures, their binding properties, etc. In addition, certain nucleotides include reactive side groups, such as sulfhydryl groups, amino groups, N-hydroxysuccinimidyl groups, that allow the further modification of nucleic acids comprising them.

An oligonucleotide sequence used as a detection probe may be labeled with a detectable moiety. Various labeling moieties are known in the art. Said moiety may, for example, either be a radioactive compound, a detectable enzyme (e.g. horse radish peroxidase (HRP)) or any other moiety capable of generating a detectable signal such as a calorimetric, fluorescent, chemiluminescent or electrochemiluminescent signal. Preferred analysis systems wherein said labels are used are electrochemiluminescence (ECL) based analysis or enzyme linked gel assay (ELGA) based analysis.

In one class of embodiments of this invention, a detectable label is incorporated into a nucleic acid during at least one cycle of the reaction. Spectroscopic, photochemical, biochemical, immunochemical, electrical, optical or chemical means can detect such labels. Useful labels in the present invention include fluorescent dyes (e.g., fluorescein isothiocyanate, Texas red, rhodamine, and the like), radiolabels (e.g., $^3$H, $^{125}$I, $^{35}$S, $^{14}$C, $^{32}$P, etc.), enzymes (e.g. horse-radish peroxidase, alkaline phosphatase etc.) calorimetric labels such as colloidal gold or colored glass or plastic (e.g. polystyrene, polypropylene, latex, etc.) beads. The label is coupled directly or indirectly to a component of the assay according to methods well known in the art. As indicated above, a wide variety of labels are used, with the choice of label depending on sensitivity required, ease of conjugation with the compound, stability requirements, available instrumentation, and disposal provisions. Non-radioactive labels are often attached by indirect means. Polymerases can also incorporate fluorescent nucleotides during synthesis of nucleic acids.

Reagents allowing the sequencing of reaction products can be utilized herein. For example, chain-terminating nucleotides will often be incorporated into a reaction product during one or more cycles of a reaction. Commercial kits containing the reagents most typically used for these methods of DNA sequencing are available and widely used. PCR exonuclease digestion methods for DNA sequencing can also be used.

Typically, the amplification sequence is serially diluted and then quantitatively amplified via the DNA Tag polymerase using a suitable PCR amplification technique. In PCR, annealing of the primers to the amplification sequence is generally carried out at about 37–50° C.; extension of the primer sequence by Taq polymerase in the presence of nucleoside triphosphates is carried out at about 70–75° C.; and the denaturing step to release the extended primer is carried out at about 90–95° C. In the two temperature PCR technique, the annealing and extension steps may both be carried at about 60–65° C., thus reducing the length of each amplification cycle and resulting in a shorter assay time.

Polymerase chain reactions (PCR) are generally carried out in about 25–50 µl samples containing 0.01 to 1.0 ng of template amplification sequence, 10 to 100 pmol of each generic primer, 1.5 units of Tag DNA polymerase (Promega Corp.), 0.2 mM DATP, 0.2 mM dCTP, 0.2 mM dGTP, 0.2 mM dTTP, 15 mM $MgCl_2$, 10 mM Tris-HCl (pH 9.0), 50 mM KCl, 1 µg/ml gelatin, and 10 µl/ml Triton X-100 (Saiki, 1988). Reactions are incubated at 94° C. for 1 minute, about 37 to 55° C. for 2 minutes (depending on the identity of the primers), and about 72° C. for about 3 minutes and repeated for about 5–40, cycles. A two temperature PCR technique differs from the above only in carrying out the annealing/extension steps at a single temperature, e.g., about 60–65° C. for about 5 minutes, rather than at two temperatures.

Quantitative methods employing PCR are known. The main constraint in obtaining accurate quantitative data is inherent in the amplification process. Because amplification is (at least initially) an exponential process, small difference in any of the variables that control the reaction rate will dramatically affect the yield of the PCR product. These variables include the concentration of polymerase, dNTPs, $Mg^2$, DNA and primers, annealing, extension and denaturing temperatures; cycle length and cycle number; ramping times; rate of "primer-dimer" formation and the presence of contaminating DNA.

Quantitation of the original target nucleic acid in the sample may be performed by a competitive PCR method to quantitatively amplify the amplification sequence, as provided, e.g., in Sambrook et al., Molecular Cloning—A Laboratory Manual, 2d Edition, Cold Spring Harbor Laboratory, 1989.

The invention comprises methods for quantitatively analyzing either an amplifiable or a self-replicating system in such a way that the amount of amplification or self-replication product is measured continuously. Continuous measurement in a PCR reaction, for example, may also mean that measurements are performed once each cycle. The method of the present invention is especially applicable for embodiments, wherein during one phase of the amplification reaction or self-replication (usually starting from the beginning or alternatively after an initial lag phase) the amount of the target product increases progressively. Moreover, the method is applicable for embodiments wherein after said exponential phase, the rate of amplification decreases.

Co-amplification of a competitive substrate is a technique used to quantitate sample. The competitive substrate functions as an internal standard. The strategy involves co-amplification of a competitive template that uses the same primers as those of the target cDNA but can be distinguished from the target cDNA after amplification. Since a change in any of the variables previously listed will affect the yield of the competitive template equally, relative ratios of the two should be preserved with amplification. The use of real time fluorescent monitoring of nucleic acid reactions has been described in U.S. Pat. No. 5,455,175.

Another embodiment of the present invention is directed to EBV-specific oligonucleotides that can be used to amplify sequences of EBV DNA, and to subsequently determine if amplification has occurred, from DNA extracted from a clinical specimen. A pair of EBV-specific DNA oligonucleotide primers are used to hybridize to EBV genomic DNA that may be present in DNA extracted from a clinical specimen, and to amplify the specific segment of genomic DNA between the two flanking primers using enzymatic synthesis and temperature cycling. Each pair of primers are designed to hybridize only to the EBV DNA to which they have been synthesized to complement; one to each strand of the double-stranded DNA. The region to which the primers have been synthesized to complement is conserved in EBV. Thus, the reaction is specific even in the presence of microgram quantities of heterologous DNA.

A nucleic acid molecule of the present invention, e.g., a nucleic acid molecule having the nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8, or a complement thereof, can be isolated using standard molecular biology techniques and the sequence information provided herein. Using all or a portion of the nucleic acid sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8, as a hybridization probe, nucleic acid sequences can be isolated using standard hybridization and cloning techniques. Furthermore, oligonucleotides can be prepared by standard synthetic techniques, e.g., using an automated DNA synthesizer.

In another embodiment, an isolated nucleic acid molecule of the invention comprises a nucleic acid molecule that is a complement of the nucleotide sequence shown in SEQ ID NO:1, SEQ ID NO:2, SEQ ID NO:3, SEQ ID NO:4, SEQ ID NO:5, SEQ ID NO:6, SEQ ID NO:7 or SEQ ID NO:8 or a portion of this nucleotide sequence. A nucleic acid molecule that is complementary to the nucleotide sequence shown in SEQ ID NO:1, SEQ ID NO:2, SEQ ID NO:3, SEQ ID NO:4, SEQ ID NO:5, SEQ ID NO:6, SEQ ID NO:7 or SEQ ID NO:8, is one that is sufficiently complementary to the nucleotide sequence shown in SEQ ID NO:1, SEQ ID NO:2, SEQ ID NO:3, SEQ ID NO:4, SEQ ID NO:5, SEQ ID NO:6, SEQ ID NO:7 or SEQ ID NO:8 that it can bind with few or no mismatches to the nucleotide sequence shown in SEQ ID NO:1, SEQ ID NO:2, SEQ ID NO:3, SEQ ID NO:4, SEQ ID NO:5, SEQ ID NO:6, SEQ ID NO:7 or SEQ ID NO:8, thereby forming a stable duplex.

A nucleic acid molecule of the invention may include only a fragment of the nucleic acid sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8. Fragments provided herein are defined as sequences of at least 6 (contiguous) nucleic acids, a length sufficient to allow for specific hybridization of nucleic acids, and are at most some portion less than a full-length sequence. Fragments may be derived from any contiguous portion of a nucleic acid sequence of choice. Derivatives are nucleic acid sequences formed from the native compounds either directly or by modification or partial substitution. Analogs are nucleic acid sequences that have a structure similar to, but not identical to, the native compound but differ from it in respect to certain components or side chains. Analogs may be synthetic or from a different evolutionary origin and may have a similar or opposite metabolic activity compared to wild type.

Derivatives and analogs may be full length or other than full length, if the derivative or analog contains a modified nucleic acid or amino acid, as described below. Derivatives or analogs of the nucleic acids of the invention include, but are not limited to, molecules comprising regions that are substantially homologous to the nucleic acids of the invention, in various embodiments, by at least about 70%, 80%, 85%, 90%, 95%, 96%, 97%, 98%, or even 99% identity (with a preferred identity of 80–99%) over a nucleic acid sequence of identical size or when compared to an aligned sequence in which the alignment is done by a computer homology program known in the art. Derivatives or analogs of the nucleic acids of the invention also include, but are not limited to, molecules comprising regions that are substantially homologous to the nucleic acids of the invention, in various embodiments, by at least about 70%, 80%, 85%, 90%, 95%, 96%, 97%, 98%, or even 99% identity (with a preferred identity of 80–99%) under stringent, moderately stringent, or low stringent conditions.

The nucleotide sequence of probes and primers typically comprises a substantially purified oligonucleotide. The oligonucleotide typically comprises a region of nucleotide sequence that hybridizes under stringent conditions to at least about 6, 9, 12, 25, or more consecutive sense strand nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8, or an anti-sense strand nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8, or of a naturally occurring mutant of SEQ ID NO:1, SEQ ID NO:2, SEQ ID NO:3, SEQ ID NO:4, SEQ ID NO:5, SEQ ID NO:6, SEQ ID NO:7 or SEQ ID NO:8.

In various embodiments, the probe further comprises a label group attached thereto. Such probes can be used as a part of a diagnostic test kit for identifying EBV infection, such as by measuring a level of an EBV nucleic acid in a sample of cells e.g., detecting EBV DNA levels in a clinical specimen of blood, cerebral-spinal fluid ("CSF"), saliva, amniotic fluid, urine, body secretions, or other body fluid and tissues.

The invention further encompasses nucleic acid molecules that differ from the nucleotide sequences shown in SEQ ID NO:1, SEQ ID NO:2, SEQ ID NO:3, SEQ ID NO:4, SEQ ID NO:5, SEQ ID NO:6, SEQ ID NO:7 or SEQ ID NO:8, due to the degeneracy of the genetic code.

In addition to the nucleotide sequence shown in SEQ ID NO:1, SEQ ID NO:2, SEQ ID NO:3, SEQ ID NO:4, SEQ ID NO:5, SEQ ID NO:6, SEQ ID NO:7 or SEQ ID NO:8, it will be appreciated by those skilled in the art that DNA sequence polymorphisms in the EBV DNA may exist within a population. Such natural allelic variations can typically result in about 1–5% variance in the nucleotide sequence of the gene. Any and all such nucleotide variations are intended to be within the scope of the invention.

Moreover, nucleic acid molecules that differ from the sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8, are intended to be within the scope of the invention. Nucleic acid molecules corresponding to natural allelic variants and homologues of the DNAs of the invention can be isolated based on their homology to the nucleic acids disclosed herein using standard hybridization techniques under stringent hybridization conditions. Preferably, such variations will differ from the sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8, by only one nucleotide.

Accordingly, in another embodiment, an isolated nucleic acid molecule of the invention is at least 6 nucleotides in length and hybridizes under stringent conditions to the nucleic acid molecule comprising the nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8.

Homologs (i.e., nucleic acids derived from other species) or other related sequences (e.g., paralogs) can be obtained under conditions of standard or stringent hybridization conditions with all or a portion of the particular sequence as a probe using methods well known in the art for nucleic acid hybridization and cloning.

In another embodiment, a nucleic acid sequence that is hybridizable to the nucleic acid molecule comprising the nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8, or fragments, analogs or derivatives thereof, under conditions of standard or stringent hybridization conditions is provided.

In addition to naturally-occurring allelic variants of the nucleotide sequence, the skilled artisan will further appreciate that changes can be introduced by mutation into the nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8.

In one embodiment, the isolated nucleic acid molecule comprises a nucleotide sequence at least about 75% homologous to the nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8. Preferably, the nucleic acid is at least about 80% homologous to the nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8, more preferably at least about 90%, 95%, 96%, 97%, 98%, and most preferably at least about 99% homologous to the nucleotide sequence of SEQ ID NO:1, SEQ ID NO:2, SEQ ID NO:3, SEQ ID NO:4, SEQ ID NO:5, SEQ ID NO:6, SEQ ID NO:7 or SEQ ID NO:8.

As already indicated above, and will be presented in the experimental part of the description, both the sensitivity and reliability of EBV mRNA detection is greatly improved using the oligonucleotides according to the present invention when compared to known oligonucleotides used in this art.

It is understood that oligonucleotides consisting of the sequences of the present invention may contain minor deletions, additions and/or substitutions of nucleic acid bases, to the extent that such alterations do not negatively affect the yield or product obtained to a significant degree.

Test kits for the detection of EBV in clinical samples are also part of the present invention. A test kit according to the invention may comprise a pair of oligonucleotides according to the invention and a probe comprising an oligonucleotide according to the invention. Such a test kit may additionally comprise suitable amplification reagents such as DNA and or RNA polymerases and mononucleotides. Test kits that can be used with the method according to the invention may comprise the oligonucleotides according to the invention for the amplification and subsequent detection of EBV mRNA. A preferred embodiment for the test kit comprises the oligonucleotides: SEQ ID NO:1 & SEQ ID NO:2; or SEQ ID NO:5 & SEQ ID NO:6 as primer pairs for the amplification, and oligonucleotides SEQ ID NO:3 or SEQ ID NO:4, for use with SEQ ID NOs:1 & 2; or SEQ ID NO:7 or SEQ ID NO:8, for use with SEQ ID NOs:3 & 4, provided with a detectable label, as probes.

A diagnostic test kit for detection of EBV according to the compositions and methods of the present invention may include, in separate packaging, a lysing buffer for lysing cells contained in the specimen; at least one oligonucleotide primer pair (SEQ ID NO:1 & SEQ ID NO:2; or SEQ ID NO:5 & SEQ ID NO:6; or both SEQ ID NO:1 & SEQ ID NO:2; and SEQ ID NO:5 & SEQ ID NO:6); enzyme amplification reaction components such as dNTPs, reaction buffer, and/or amplifying enzyme; and at least one oligonucleotide probe labeled with a detectable moiety (SEQ ID NO:3 or SEQ ID NO:4, for use with SEQ ID NOs:1 & 2; or SEQ ID NO:7 or SEQ ID NO:8, for use with SEQ ID NOs:3 & 4), or various combinations thereof.

The present invention further provides nucleic acid detection kits, including arrays or microarrays of nucleic acid molecules that are based on one or more of the sequences provided in SEQ ID NO:1, SEQ ID NO:2, SEQ ID NO:3, SEQ ID NO:4, SEQ ID NO:5, SEQ ID NO:6, SEQ ID NO:7 and SEQ ID NO:8. As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., In other embodiments, such arrays are produced by the methods described by Brown et al., U.S. Pat. No. 5,807,522. The oligonucleotides are generally about 5–35 nucleotides in length, preferably about 10–30 nucleotides in length and more preferably about 18–26 nucleotides in length. For a certain type of microarray or detection kit, it may be preferable to use oligonucleotides that are only 4–18 nucleotides in length.

It should be understood that while the invention has been described in detail herein, the examples were for illustrative purposes only. Other modifications of the embodiments of the present invention that are obvious to those of ordinary skill in the art of molecular biology, medical diagnostics, and related disciplines are intended to be within the scope of the appended claims.

The invention will be further illustrated in the following non-limiting examples.

EXAMPLES

The invention is further illustrated in the following examples, which are not intended to be in any way limiting to the scope of the invention as claimed.

Experimental

Quantitative EBV Assay for the LIGHTCYCLER®

The present invention, a quantitative EBV assay, is capable of amplifying EBV genomic DNA from samples and can detect down to a level of 3–4 copies of EBV genome per test sample.

The results [not shown] typically show a range of detectable EBV DNA levels using a series of sample dilutions from a known source of EBV virus (EBV B95-8, Advanced Biotechnologies Incorporated Columbia Md.). Also included in the test samples is one patient sample showing >3,000 copies of EBV.

These levels are followed at biweekly intervals for 3 months after documentation of the initial infection, then monthly intervals for 1 year followed by yearly checks. If at anytime during this time course there is reactivation of the EBV infection the blood monitoring may be increased in frequency.

During the past year 204 patient blood samples from patients were evaluated to determine the EBV copy number based on the assay described herein. The blood samples were obtained from a mixture of pediatric age patients, some of which were immunocompromised, including organ transplant patients, oncology patients undergoing cytotoxic chemotherapy, patients with inborn genetic defects in their immune system, and at high risk for EBV infection and others who are immunocompetent. All blood samples were submitted at the request of the attending physician for diagnostic EBV PCR studies (Diasorin/Incstar, Stillwater, Minn.). Samples were split, and run in parallel to compare the results of the qualitative Diasorin assay with the present method. A high degree of correlation was found when comparing the two assays for validation purposes. The tables I and II represent the total number of patient samples that were validated against each other.

TABLE 1

| Date of Sample | Quantitative Results |
|---|---|
| Patient I | |
| Feb. 18, 2000 | 0.00 |
| Feb. 24, 2000 | 0* |
| Mar. 8, 2000 | 404.00 |
| Mar. 15, 2000 | 36740.00 |
| Apr. 5, 2000 | 120.00 |
| Apr. 11, 2000 | 0.00 |
| Apr. 17, 2000 | 0.00 |
| Jun. 6, 2000 | 3000.00 |
| Jun. 10, 2000 | 63040.00 |
| Jun. 14, 2000 | 3920.00 |
| Patient II | |
| Aug. 23, 2000 | 5640.00 |
| Aug. 24, 2000 | 2320.00 |
| Aug. 30, 2000 | 1230.00 |
| Sep. 7, 2000 | 40.00 |
| Apr. 11, 2000 | 0.00 |
| Apr. 17, 2000 | 0.00 |
| Jun. 6, 2000 | 3000.00 |
| Jun. 10, 2000 | 63040.00 |
| Jun. 14, 2000 | 3920.00 |
| Patient III | |
| Apr. 11, 2000 | 0.00 |
| Apr. 21, 2000 | 0.00 |
| May 4, 2000 | 327.30 |
| May 22, 2000 | 1677.00 |
| May 27, 2000 | 1837.00 |

TABLE II

| | Positive | Negative | Equivocal |
|---|---|---|---|
| Qualitative Results (Diasorin Assay) | 125 | 66 | 14* |
| Quantitative Results | 129/6 | 75/8 | 0 |

*O.D. reading < 0.600

Patient results listed in the equivocal column in the qualitative (Diasorin/Incstar, Stillwater, Minn.) assay are based on results that were greater than the negative O.D. cutoff point (0.50) but less than 0.60 reading. No PCR inhibition was observed in samples with negative test results. To evaluate the specificity of the assay, a panel of 20 samples known to be positive for a variety of viral pathogens was also evaluated by the present assay. These samples included the following viral pathogens: adenovirus, cytomegalovirus, herpes simplex, enterovirus, and parvovirus.

None of these samples showed cross reaction with the present assay described below.

Reproducibility

The performance of the assay at different concentration ranges was determined using EBV B95-8, (Advanced Biotechnologies Incorporated Columbia Md.). Ten identical samples with 10,000 copies and ten identical samples with 5,000 copies were analyzed simultaneously. The target sequence was detected with specific hybridization probes as described below. The results show that 5,000 and 10,000 copies could be clearly differentiated and the coefficient of variation of less than 7.5% was obtained for a series of identical samples with less than 100 copies.

Listed above are the results of assays using the quantitative EBV assay described herein. All three examples represent analyses performed sequentially over a period of time, as indicated in the graphs, on patients who were immunosuppressed, and at high risk for developing EBV lymphoproliferative disease. Patient I was a bone marrow transplant patient who exhibited a bimodal elevation of EBV copy numbers in the peripheral blood with a range from 0.0 to more than 63,000 copies over a 4-month period. These bimodal peak levels corresponded with two periods of immunosuppressive therapy for graft versus host disease during which time the patient was highly immunosuppressed.

During the interval between peak levels, immunosuppressive therapy was withdrawn and associated with a drop in EBV copy numbers. Patient II represents an immunosuppressed bone marrow transplant patient who was initially monitored during an episode of biopsy proven active EBV lymphoproliferative disease. Therapeutic intervention to control the EBV infection and restore immunocompetence was instituted which was associated with the fall in EBV copy levels as shown in the graph from an initially high level of greater than 5,000 to less than 50 copies. Patient III shows a rise in EBV copy number from a baseline of 0.0 to more than 1800 during a 6 week time period. This patient was a liver transplant recipient who during the time period illustrated in graph number III was being treated aggressively for transplant rejection with high dose immunosuppression.

Materials for Assay

Equipment: LIGHTCYCLER® Instrument (Roche Diagnostics, Mannheim, Germany) with Oligo Software.

Reagents: Amplification Primers (University of Cincinnati DNA Core Facility); Hybridization Probes (Genset); Qiagen Digestion Kit (Qiagen); FastStart LIGHTCYCLER® DNA Master Hybridization Probes; LIGHTCYCLER® Control Kit DNA; Advanced Biotechnologies Inc (EBV viral DNA)

Assay Procedure

Viral DNA was prepared, using the Qiagen whole blood digestion kit according to the manufacture's instructions. Starting with 200 µl of whole blood, 20 µl of Proteinase K (20 mg/ml) was added then 200 µl of a lysis buffer. Samples were then incubated for about 10 minutes at about 56° C. The samples are then ran over a spin column, washed and then eluted with a Tris-EDTA solution. The eluted product was used directly in a PCR reaction without any further treatment. From 1 ml of whole blood were acquired about 10.0 µg of genomic DNA. The LIGHTCYCLER® reaction runs with 1100 ng of genomic DNA, which is approximately 2 µl of digested sample.

The EBV genome is a 170-kilobase linear DNA molecule that consists of largely unique DNA domains(U1,U2,U3,U4, and U5), as shown in FIG. 1, with internal tandem direct repeats (IR1, IR2, IR3, IR4), and terminal repeats (TR). In latently infected cells, the complete viral genome is limited. persists as episomes or integrated DNA. The expression of viral genome However at least three sites on the viral genome are characteristically transcribed:

I. IR1 into U2

II. U3 through IR3 into U4

III. From U5

This protocol is set up to amplify the EBNA 2 region using primers shown in Table III.

TABLE III

| | Position | Length | GC (%) | Tm (C) |
|---|---|---|---|---|
| Primers | | | | |
| GGCTGGTGTCACCTGTTA (SEQ. ID. NO.1) | 90030:90049 | 18 | 55 | 50 |
| CCTTTAGGAGGAAGAAGTCCC (SEQ. ID. NO.2) | 90249:90269 | 20 | 55 | 50 |
| Product | 90030:90269 | 239 | | |
| Hybridization Probes | | | | |
| GGTGGAGGGCTGAGTGTCTCTGGGT-F red 640 (SEQ. ID. NO.3) | 90114:90139 | 25 | 64 | 71.8 |
| GAACTGGGTGTGAGTGACATGGAAGA-p (SEQ. ID. NO.4) | 90142:90167 | 26 | 50 | 66.9 |

Other sequences that may be used include:

Primers:

(sense)      AGGGATGCCTGGACACAAGA      (SEQ. ID. NO.5)

(antisense) ATTGCCACCACCAGCAGCACCA    (SEQ. ID. NO.6)

Probes (1)          CATCTGCTATGCGAATGCTTTG    (SEQ. ID. NO.7)

(2)          GCTAATTATATTGTAAGACA      (SEQ. ID. NO.8)

LIGHTCYCLER PCR

The master mix shown in Table IV was used for amplification and hybridization probe-based detection of the Epstein Barr specific amplicon.

TABLE IV

Epstein Barr Virus Master Mix

|  | Volume (µl) | Final concentration |
|---|---|---|
| Sterile water | 4.9 | |
| MgCl$_2$ stock solution | 2.4 | 4.0 mM |
| Primer 1 | 1.4 | 0.5 µM |
| Primer 2 | 1.6 | 0.5 µM |
| Red Probe | 2.5 | 0.4 µM |
| Flour. Probe | 3.2 | 0.175 µM |
| LIGHTCYCLER enzyme | 2 | 1 X |

To complete the amplification mixtures, 18 µl of master mix and 2 µl (10 ng) of the corresponding template DNA preparation were added to each capillary. After a short centrifugation, the sealed capillaries were placed into the LIGHTCYCLER® rotor.

The negative PCR control sample was prepared by replacing the DNA template with PCR grade water. Another negative control that was used was genomic DNA that was provided with the β-globulin kit. A positive control sample was purchased from Advanced Biotech.

The following PCR protocol was used for amplification and Hybridization probe-based detection of the Epstein Barr specific amplicons using the parameters of Table V.

Denaturation for 10 minutes at 95° C.

Amplification

TABLE V

| PARAMETER Cycles | VALUE Quantification | | |
|---|---|---|---|
| Type | Segment 1 | Segment 2 | Segment 3 |
| Target temperature (° C.) | 95 | 52 | 72 |
| Incubation time (s) | 10 | 15 | 10 |
| temperature transition rate (C/s) | 20 | 20 | 20 |

TABLE V-continued

| Acquisition mode | None | Single | None |
|---|---|---|---|
| Gains | F1-1, F2-15, F3-30 | | |

Cooling for 2 minutes at 40° C.
Copy Number Calculation

The amplification curves were obtained by the previous procedure for single color detection using LIGHTCYCLER®-Red 640 as acceptor flourophore. The LIGHTCYCLER® software allows the full log-linear region of the amplification. To minimize extrapolation error the log lines are extrapolated to the noise band line which define the beginning of the log-linear phase. A standard curve is constructed by plotting the crossing points against the common logarithm of standards copy number. The copy number of unknown samples is calculated by interpolation of the standard curve.

The development and implementation of this assay can provide a highly sensitive, accurate, more rapid quantitative PCR assay to detect EBV copies in this population of patients who are at high risk to develop serious and costly medical complications and hopefully allow for better clinical management of these patients by earlier recognition of their infection status.

The present assay has a broad dynamic range of detection from <10 to 10,000,000 copies of EBV DNA, is less labor intensive requiring only one reaction tube for the EBV determination, and has a rapid turn around time with assays that are completed, including amplification, probe specific hybridization, and calculation of copy number in less than 1 hour. The methods of the present invention may be adapted to automated systems such as the MagnaPure system by Roche.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated and purified oligonucleotide primer pair for enzymatic amplification of Epstein-Barr virus DNA, consisting essentially of a pair of nucleic acid sequences which complement and specifically hybridize to a nucleic acid sequence of an Epstein-Barr virus under stringent conditions, which encodes a conserved EBNA2 region of the Epstein-Barr virus genome, wherein the pair of nucleic acid sequences is at least 95% homologous to sequences of SEQ ID NO: 1 and SEQ ID NO: 2, respectively.

2. An isolated and purified oligonucleotide primer pair for enzymatic amplification of Epstein-Barr virus DNA, consisting essentially of a pair of nucleic acid sequences which complement and specifically hybridize to a chromosomal gene of an Epstein-Barr virus under stringent conditions, and which encodes a conserved EBNA2 region of the Epstein-Barr virus genome, wherein the pair of nucleic acid sequences is selected from the group consisting of (a) the oligonucleotide pair of SEQ ID NO: 1 and SEQ ID NO:2, and (b) a primer pair, which differs from SEQ ID NO: 1 and SEQ ID NO: 2 by a one base change or substitution therein, and (d).

3. A method of detecting the presence of Epstein Barr virus DNA in a sample comprising: a) contacting the sample with oligonucleotide primer pair of SEQ ID NO. 1 and SEQ ID NO: 2 under suitable conditions permitting hybridization of the oligonucleotides to the Epstein Barr virus DNA, b) enzymatically amplifying a region of the Epstein Barr virus DNA using the oligonucleotide pair SEQ ID NO: 1 and SEQ ID NO: 2 to form nucleic acid amplification products, c)

contacting the amplified Epstein Barr virus DNA sequences from step (b), if present, with hybridization probes comprising the oligonucleotide pair of SEQ. ID. NO. 3 and SEQ. ID. NO. 4 or the oligonucleotide pair of SEQ. ID. NO. 7 and SEQ. ID. NO. 8, labeled with a detectable moiety under suitable conditions permitting hybridization of the labeled oligonucleotide probe to amplified Epstein Barr virus DNA sequences, and d) detecting the presence of amplified Epstein Barr virus DNA sequences by detecting the detectable moiety of the labeled oligonucleotide probe hybridized to the amplified Epstein Barr virus DNA sequences.

4. The method of claim 3, wherein the sample is treated to release nucleic acid molecules from cells in the sample prior to step (a).

5. The method of claim 3, wherein the presence of the amplified Epstein Barr virus DNA sequences hybridized to labeled oligonucleotide probe correlates to the presence of Epstein Barr virus in the sample.

6. The method of claim 5, wherein the amplified DNA sequences are from the EBNA2 region of the Epstein Barr virus genome.

7. The method of claim 5, additionally comprising adding an internal standard for accessing relative amounts of Epstein Barr virus after amplification.

8. The method of claim 5, wherein presence of the amplified Epstein Barr virus DNA sequences hybridized to labeled oligonucleotide probe is correlated to the presence of Epstein Barr virus in the sample by comparing the amount of amplification product to the quantity of amplification products formed from known internal standards.

9. The method of claim 5, wherein the amplification is performed by cyclic polymerase-mediated reaction.

10. The method of claim 9, wherein the cyclic polymerase-mediated reaction is an enzymatic assay selected from the group consisting of PCR, LCR, SDA, QβRA, 3SR, and NASBA.

11. The method of claim 10, wherein the polymerase is selected from the group consisting of thermostable polymerase, E. coli DNA pol I, Klenow fragment, and T7 DNA polymerase.

12. The method of claim 11, wherein the PCR is a thermocyclic reaction.

13. The method of claim 5, wherein the detectable moiety is selected from the group consisting of a digoxigenin-dUTP, biotin, calorimetric, fluorescent, chemiluminescent, electrochemiluminescent signal and a radioactive component.

14. The method of claim 5, wherein the detectable moiety is a fluorescent component generating a fluorescent signal.

15. The method of claim 11, the amount of amplification product is determined simultaneously with respect to the PCR amplification step.

16. A method of selecting an appropriate dosage or type of antiviral agent for treating an infection caused by Epstein Barr virus comprising the steps of: a) obtaining a sample from a patient to be treated; b) preparing the sample for PCR amplification; c) adding PCR reagents to the prepared sample, including one primer pair SEQ ID NO: 1 and SEQ ID NO: 2 and complementary sequences thereof; d) maintaining the prepared sample of step c under conditions suitable for amplification; e) adding at least one probe labeled with a detectable moiety corresponding to the primer pair, selected from the group consisting of the oligonucleotide pair of SEQ. ID. NO. 3 and SEQ. ID. NO. 4, the oligonucleotide pair of SEQ. ID. NO. 7 and SEQ. ID. NO. 8, and complementary sequences thereof, under suitable conditions permitting hybridization; f) measuring quantitatively one or more of the Epstein Barr virus species contained in the sample; and vii) selecting the type or adjusting the dosage of the antiviral agent based on the quantitative measurement.

17. The method of claim 16 additionally comprising adding to step c) an internal standard for accessing relative amounts of Epstein Barr virus after amplification.

18. The method of claim 17, wherein the PCR reagents comprise a polymerase selected from the group consisting of thermostable polymerase, E. coli DNA pol I, Klenow fragment, and T7 DNA polymerase.

19. The method of claim 18, wherein the detectable moiety is selected from the group consisting of a digoxigenin-dUTP, biotin, calorimetric, fluorescent, chemiluminescent, electrochemiluminescent signal and a radioactive component.

20. The method of claim 10, further comprising a separation step wherein the amplified product is isolated.

21. A method for the simultaneous amplification and detection of Epstein Barr Virus DNA in a sample comprising: a) processing the sample to produce denatured opposing strands of DNA; b) simultaneously subjecting the denatured opposing strands of DNA to polymerase chain reaction in the presence of: i) an aqueous solution buffered to a pH of about 6 to about 9; and ii) first and second primers which are specific to and hybridizable with the denatured opposing strands of DNA, wherein the sequences of the first and second primers are SEQ ID NO: 1 and SEQ ID NO: 2 and c) simultaneously detecting the amplified DNA using hybridization probes comprising the oligonucleotide pair of SEQ. ID. NO. 3 and SEQ. ID. NO. 4 or the oligonucleotide pair of SEQ. ID. NO. 7 and SEQ. ID. NO. 8.

22. The method of claim 21 wherein the hybridization probe further comprises a detectable moiety selected from the group consisting of a chemiluminescent component, a fluorescent component, and a radioactive component.

23. A diagnostic test kit for detection of Epstein Barr virus comprising: (a) at least one oligonucleotide primer pair SEQ ID NO: 1 and SEQ ID NO: 2 and both the oligonucleotide pair and (b) at least one oligonucleotide probe labeled with a detectable moiety selected from the group consisting SEQ. ID. NO. 3, SEQ. ID. NO. 4, SEQ. ID. NO. 7 and SEQ. ID. NO. 8.

24. The diagnostic test kit of claim 23, further comprising at least one additional reagent selected from the group consisting of a lysing buffer for lysing cells contained in the specimen; enzyme amplification reaction components dNTPs, reaction buffer, and amplifying enzyme; and a combination thereof.

25. The diagnostic kit of claim 23, wherein the hybridization probe further comprises a detectable moiety selected from the group consisting of a chemiluminescent component, a fluorescent component, and a radioactive component.

* * * * *

SEQUENCE LISTING

```
<160> NUMBER OF SEQ ID NOS: 8
<210> SEQ ID NO 1
<211> LENGTH: 18
<212> TYPE: DNA
<213> ORGANISM: Human herpesvirus 4

<400> SEQUENCE: 1
ggctggtgtc acctgtta                                                 18

<210> SEQ ID NO 2
<211> LENGTH: 20
<212> TYPE: DNA
<213> ORGANISM: Human herpesvirus 4

<400> SEQUENCE: 2
ccttaggagg aacaagtccc                                               20
```

-continued

```
<210> SEQ ID NO 3
<211> LENGTH: 25
<212> TYPE: DNA
<213> ORGANISM: Human herpesvirus 4

<400> SEQUENCE: 3
ggtggagggc tgagtgtctc tgggt                                    25

<210> SEQ ID NO 4
<211> LENGTH: 26
<212> TYPE: DNA
<213> ORGANISM: Human herpesvirus 4

<400> SEQUENCE: 4
gaactgggtc tcagtgacat ggaaga                                   26

<210> SEQ ID NO 5
<211> LENGTH: 20
<212> TYPE: DNA
<213> ORGANISM: Human herpesvirus 4

<400> SEQUENCE: 5
agggatgcct ggacacaaga                                          20

<210> SEQ ID NO 6
<211> LENGTH: 22
<212> TYPE: DNA
<213> ORGANISM: Human herpesvirus 4

<400> SEQUENCE: 6
attgccacca ccagcagcac ca                                       22

<210> SEQ ID NO 7
<211> LENGTH: 22
<212> TYPE: DNA
<213> ORGANISM: Human herpesvirus 4

<400> SEQUENCE: 7
catctgctat gcgaatgctt tg                                       22

<210> SEQ ID NO 8
<211> LENGTH: 20
<212> TYPE: DNA
<213> ORGANISM: Human herpesvirus 4

<400> SEQUENCE: 8
gctaattata ttgtaagaca                                          20
```